United States Patent [19]
Oppong et al.

[11] Patent Number: 5,728,730
[45] Date of Patent: Mar. 17, 1998

[54] SYNERGISTIC ANTIMICROBIAL COMPOSITIONS CONTAINING METHYLENE-BIS(THIOCYANATE) AND AN ORGANIC ACID

[75] Inventors: David Oppong; Vanja M. King, both of Memphis, Tenn.

[73] Assignee: Buckman Laboratories International, Inc., Memphis, Tenn.

[21] Appl. No.: 810,705

[22] Filed: Mar. 3, 1997

Related U.S. Application Data

[62] Division of Ser. No. 668,227, Jun. 21, 1996, Pat. No. 5,633,278, which is a division of Ser. No. 468,664, Jun. 6, 1995, Pat. No. 5,530,024, which is a division of Ser. No. 187,075, Jan. 27, 1994, Pat. No. 5,441,979.

[51] Int. Cl.$^6$ .................... A01N 37/00; A01N 47/48
[52] U.S. Cl. .................. 514/515; 514/514; 514/557; 514/558; 514/574; 514/560
[58] Field of Search .................... 514/574, 557, 514/558, 560, 515, 514

[56] References Cited

U.S. PATENT DOCUMENTS

| | | | |
|---|---|---|---|
| 3,231,509 | 1/1966 | Shema | 252/177 |
| 3,426,134 | 2/1969 | Shema et al. | 514/515 |
| 3,524,871 | 8/1970 | Matt | 260/454 |
| 3,595,665 | 7/1971 | Huitson et al. | 99/8 |
| 3,674,457 | 7/1972 | Wolfson | 71/67 |
| 4,616,037 | 10/1986 | LaMarre et al. | 514/515 |
| 4,835,144 | 5/1989 | Whitekettle et al. | 514/515 |

FOREIGN PATENT DOCUMENTS

| | | |
|---|---|---|
| 0339957 | 11/1989 | European Pat. Off. |
| 0488606 | 6/1992 | European Pat. Off. |
| 1084154 | 9/1967 | United Kingdom |
| WO 92/19104 | 11/1992 | WIPO |

OTHER PUBLICATIONS

The Merck Index, 10th Ed. (1983), pp. 155, 156, 700, and 1200.

Weber et al., Chemical Abstracts, vol. 98, 98:174, 866a (1983).

The Merck Index, 11th Ed. (1989), pp. 450, 1217, and 1375.

*Primary Examiner*—Allen J. Robinson
*Attorney, Agent, or Firm*—Armstrong, Westerman, Hattori, McLeland & Naughton

[57] ABSTRACT

Compositions for controlling the growth of microorganisms in or on a product, material or medium comprising synergistically effective amounts of methylene-bis(thiocyanate) and at least one organic acid, its salt or ester are disclosed. Methods to control the growth of microorganisms and prevent spoilage caused by microorganisms with the use of the compositions of the present invention are also disclosed.

37 Claims, No Drawings

SYNERGISTIC ANTIMICROBIAL COMPOSITIONS CONTAINING METHYLENE-BIS(THIOCYANATE) AND AN ORGANIC ACID

This is a division of application Ser. No. 08/668,227, filed Jun. 21, 1996, now U.S. Pat. No. 5,633,278, which was a division of application Ser. No. 08/468,664, filed Jun. 6, 1995, now U.S. Pat. No. 5,530,024; which was a division of application Ser. No. 08/187,075, filed Jan. 27, 1994, now U.S. Pat. No. 5,441,979.

The present invention relates to certain compositions and processes useful for controlling the growth of one or more microorganisms and for preventing spoilage caused by bacteria and fungi in various products, materials or media, particularly industrial products, materials or media. These products, materials or media include paints, leather, wood, wood pulp, wood chips, starch, proteinaceous materials, lumber, animal hides, vegetable tanning liquors, cosmetics, toiletry formulations, acrylic latex paint emulsions, adhesives, coatings, metalworking fluids, cooling tower water, textiles, petrochemicals, pharmaceutical formulations, geological drilling lubricants, paper mill liquors, and agrochemical compositions.

The novel compositions and processes incorporating the composition of the present invention show unexpected, synergistic activity against microorganisms, including bacteria and fungi. Specifically, the invention is directed to the use of compositions and processes containing methylene-bis(thiocyanate) and at least one organic acid, its salt or ester.

Many of the products, materials or media referred to above when wet or subjected to treatment in water, are susceptible to bacterial and/or fungal deterioration or degradation unless steps are taken to inhibit such degradation or deterioration. To control deterioration or degradation caused by microorganisms, various industrial microbicides are used, but some of these biocides are of questionable utility because they have undesirable odors, are high in cost, show a low degree of effectiveness and/or create hazards with respect to storage, use and/or handling.

For instance, the use of such popular industrial microbicides as organomercury compounds, organotin compounds and chlorinated phenols has come under increasing regulatory pressure in recent times because of their high toxicity and concern about their adverse effects on the environment. Consequently, the industry has continued to seek improved biocides that have low toxicity and are capable of exhibiting prolonged biocidal effect at normal use levels.

Organic acids can be used alone to control microorganisms, and while some of these compounds are generally regarded as safe, many of them have low efficacy against bacteria and fungi unless extremely high concentrations are used. In excessive concentrations, these organic acids can be expensive and could even be corrosive to certain industrial materials. A method that can prevent excessive use of organic acids and hence decrease cost is therefore desirable.

Alternatively, methylene-bis(thiocyanate) can be used alone in low concentrations as low toxicity biocides. However, at low concentrations, methylene-bis(thiocyanate) tends to have a narrow antimicrobial spectrum and fails to completely prevent the growth of microorganisms.

Accordingly, the present invention is directed to microbicidal compositions and processes incorporating these compositions that substantially obviate one or more of the problems, limitations, and disadvantages of the prior art. In particular, the compositions of the present invention are capable of controlling the growth of at least one microorganism, especially fungi or bacteria, over prolonged periods of time, and are safe and economical to use. The present invention also is directed to methods or processes of controlling the growth of at least one microorganism.

The present invention provides a composition to control the growth of at least one microorganism comprising synergistically effective amounts of methylene-bis(thiocyanate) and at least one organic acid, its salt or ester. The composition provides superior microbicidal activity at low concentrations against a wide range of microorganisms.

The present invention also provides a method for controlling the growth of at least one microorganism in or on a material or medium susceptible to attack by the microorganism which comprises the step of adding to the material or medium a composition of the present invention, where the components of the composition are present in synergistically effective amounts.

Furthermore, the present invention provides a method of preventing spoilage of a product, material or medium caused by bacteria and/or fungi comprising the step of adding to the product, material or medium, a composition of the present invention where the components of the composition are present in synergistically effective amounts.

The synergistically effective amounts vary in accordance with the material or medium to be treated and can, for a particular application, be routinely determined without undue experimentation by one skilled in the art.

The present invention also embodies the separate addition of methylene-bis(thiocyanate) and at least one organic acid, its salt or ester to the products, materials or media described above. According to this embodiment, the components are individually added to the system so that the final amount of methylene-bis(thiocyanate) and at least one organic acid, its salt or ester present in the system at the time of use is that synergistically effective amount required to control the growth of at least one microorganism.

The compositions of the present invention are also useful in preserving various types of industrial products, media or materials that are susceptible to attack by microorganisms. Such products, media or materials include but are not limited to dyes, pastes, lumber, leather, textiles, pulp, wood chips, tanning liquors, paper mill liquors, polymer emulsions, paints, paper and other coating and sizing agents, metalworking fluids, geological drilling lubricants, petrochemicals, cooling water systems, pharmaceutical formulations, cosmetics and toiletry formulations.

The compositions can also be useful in agrochemical formulations for the purpose of protecting seeds or crops against microbial spoilage.

Additional advantages of the invention will be set forth in part in the description which follows, and in part will be obvious from the description, or may be learned by the practice of the invention. The advantages of the invention may be realized and obtained by means of the elements and combinations particularly pointed out in the claims.

It is to be understood that both the foregoing general description and the following detailed description are exemplary and explanatory only and are not restrictive of the present invention as claimed.

When two chemical microbicides are combined into one product or added separately three results are possible:

1) The chemicals in the product would produce an additive (neutral) effect.
2) The chemicals in the product would produce an antagonistic (negative) effect, or 3) The chemicals in the product would produce a synergistic (positive) effect.

An additive effect has no economic advantage over the individual components. The antagonistic effect would produce a negative impact. Only a synergistic effect, which is less likely than either an additive or antagonistic effect, would produce a positive effect and therefore possess economic advantage.

It is well-known in the microbicidal literature that there is no theoretical method to provide the likelihood of knowing, before actually testing, whether additive, antagonistic or synergistic effects will be obtained when two biocides are mixed to yield a formulation.

The microbicidal compositions combining methylene-bis(thiocyanate) and at least one organic acid, its salt or ester demonstrate an unexpected, synergistic effect compared to the respective components alone. Thus these compositions achieve superior, i.e. greater than additive microbicidal activity at low concentrations against a wide variety of microorganisms. Examples of microorganisms include fungi and bacteria such as, but not limited to, *Trichoderma hazianum* and *Pseudomonas aeruginosa*. These two organisms are some of the most common organisms associated with spoilage of products, materials or media. Since these two are also some of the toughest organisms to control, the composition of the present invention is believed to be effective against most bacteria and fungi. Preferably, the compositions of the present invention have a low toxicity.

The preparation of methylene-bis(thiocyanate) (MTC) is described in U.S. Pat. No. 3,524,871, which disclosure is fully incorporated by reference. MTC is commercially available and also easily synthesized from commercially available raw materials. A preferred MTC according to the present invention is 2-methylene-bis(thiocyanate).

The organic acids of the present invention are any organic acid that produce a synergistic effect when combined with the MTC. Examples of organic acids include aromatic organic acids, cyclic organic acids, aliphatic organic acids, their salts or esters. Specific examples of effective organic acids according to the invention include dehydroacetic acid, octanoic acid, nonanoic acid, formic acid, sorbic acid, acetic acid, oxalic acid, glycolic acid, citric acid, gluconic acid, malic acid, propionic acid, lauric acid, undecylenic acid, benzoic acid or derivatives of benzoic acid such as 2-hydroxybenzoic acid, 3-hydroxybenzoic acid or 4-hydroxybenzoic acid, methyl paraben or propyl paraben.

The salts of the organic acids, preferably those containing calcium, zinc, potassium, or sodium, may be used, such as sodium benzoate and potassium sorbate. Preferred esters are parabens such as methyl paraben and propyl paraben.

In accordance with the present invention, mixtures of these organic acids, salts or esters can also be used. When such mixtures are used in combination with MTC, at least one of the organic acids in the mixtures has a synergistic relationship with MTC. Organic acids, salts and esters useful in the invention are commercially available or may be synthesized from commercially available raw materials.

The organic acid may be chosen, for example, based on the compatibility of the acid with the products, materials or media. The compatibility is readily determined by adding the organic acid to the products, materials or media to be used.

Compatibility may be determined by criteria such as solubility in a fluid system and/or lack of reactivity with the fluid in question. When used in a fluid system, for example, it is preferable that the organic acid be freely soluble or dispersible in the particular fluid system, resulting in a uniform solution or dispersion. Examples of fluid systems are tanning liquor, paper mill liquor, cooling tower water, and paints.

In accordance with the present invention, the composition may be in the form of a solid, dispersion, emulsion or solution, depending on the particular application. Further, the components of the composition may be applied separately or may be combined first and then applied to the product, material or medium. The composition of the present invention may be prepared in liquid form by dissolving components (A) and (B) in an organic solvent.

In the following discussion of preferred embodiments, component (A) is 2-methylene-bis(thiocyanate) and component (B) is at least one organic acid, its salt or ester.

As described above, components (A) and (B) of the composition are used in synergistically effective amounts. The weight ratios of (A) to (B) vary depending on the type of microorganisms, as well as the products, materials or media to which the composition is applied. One skilled in the art can readily determine the appropriate weight ratios for a specific application.

In the present invention, the weight ratio of component (A) to component (B) preferably ranges from about 0.01:99 to about 99:0.01, more preferably from about 1:30 to about 30:1, and most preferably about 1:5 to about 5:1.

The following approximate range of weight ratios of MTC to the following organic acids are also preferred according to the present invention:

MTC: benzoic acid 1:5 to 0.1:100
MTC: sodium benzoate 1:100 to 0.1:400
MTC: methyl paraben 1:5 to 0.01:100
MTC: propyl paraben 1:5 to 0.01:100
MTC: p-hydroxybenzoic acid 1:5 to 0.1:250
MTC: dehydroacetic acid 1:5 to 1:400
MTC: octanoic acid 1:5 to 1:400
MTC: nonanoic acid 1:10 to 1:400
MTC: formic acid 1:50 to 1:800
MTC: sorbic acid 1:5 to 0.1:100
MTC: potassium sorbate 1:5 to 1:800
MTC: acetic acid 1:100 to 1:200
MTC: oxalic acid 1:50 to 1:200
MTC: glycolic acid 1:100 to 1:400
MTC: citric acid 1:100 to 1:400
MTC: malic acid 1:100 to 1:400
MTC: propionic acid 1:10 to 1:400
MTC: lauric acid 1:5 to 0.1:400
MTC: undecylenic acid 1:5 to 0.1:500

In general, however, an effective fungicidal and bactericidal response can be obtained when the synergistic combination is employed in concentrations ranging from about 0.01 to about 3000 ppm of methylene-bis(thiocyanate), preferably from about 0.1 to about 1000 ppm, and most preferably from about 0.1 to about 500 ppm, and from about 0.1 ppm to about 1% by weight of the organic acid, preferably from about 0.1 to about 5000 ppm, and most preferably from about 0.1 to about 2000 ppm.

The present invention also provides a method for controlling the growth of at least one microorganism in or on a material or medium susceptible to attack by the microorganism which comprises the step of applying to the material or medium a composition of the present invention, where the components of the composition are present in synergistically effective amounts.

Furthermore, the present invention provides a method of preventing spoilage of a product, material or medium caused by bacteria and/or fungi comprising the step of applying to said product, material or medium, a composition of the present invention where the components of the composition are present in synergistically effective amounts. For example, the composition may be used to prevent the spoilage of seeds or crops, e.g. cotton, barley, rice, maize, tobacco, etc.

The mode and rate of application of the composition varies depending upon the intended use of the composition. For instance, the composition may be applied by spraying or brushing onto a material or product. The material or product could also be treated by dipping in a suitable formulation of the composition. For a liquid or liquid-like medium, the composition could be added into the medium by pouring, or by metering with a suitable device, so that a solution or a dispersion containing the composition is produced. If used as a liquid preservative, for example, the composition may be prepared as an aqueous emulsion. If necessary, a surfactant may be added to the composition.

In accordance with the invention, additional components such as insecticides and the like may be added to the foregoing preparations without affecting the synergistic effects of the composition. Insecticides that may be used include but are not limited to pyrethrins, nicotine, chlordane, parathions, and methoxychlor.

The synergistic activity of the combinations described above has been confirmed using standard laboratory techniques, as illustrated below. The following examples are intended to illustrate, not limit, the scope of the present invention.

Microbiological evaluation

A. Fungal evaluation

A mineral salts-glucose medium was first prepared by adding to 1 liter of deionized water: 0.7 g of $KH_2PO_4$, 0.7 g of $MgSO_4 \cdot 7H_2O$, 1.0 g of $NH_4NO_3$, 0.005 g NaCL, 0.002 g $FeSO_4 \cdot 7H_2O$, 0.002 g $ZnSO_4 \cdot 7H_2O$, 0.001 g $MnSO_4 \cdot 7H_2O$, and 10 g of Glucose. The pH of the medium was adjusted to 6 with 1N NaOH. The medium was then dispensed in 5 mL amounts into test tubes and autoclaved at 121° C. for 20 minutes.

The fungus, *Trichoderma harzianum*, was grown on a potato dextrose agar slant for 7 to 10 days and a spore suspension prepared by washing down the spores from the slant into a sterile saline solution. After the addition of biocides in the desired concentrations to the sterile mineral salts-glucose medium, the fungal spore suspension was added. The final spore concentration was approximately $10^6$ cfu/mL. The inoculated media was incubated at 28° C. for 14 days.

B. Bacterial evaluation

Nutrient broth (2.5 g/liter of deionized water) was prepared and the pH adjusted to 6 with 1N HCL. This was dispensed in 5 mL amounts into test tubes and autoclaved for 20 minutes at 121° C. After the addition of biocides in the desired concentrations to the nutrient broth, 100 microliters of a suspension of *Pseudomaeas aeruginosa* cells of approximately $9.3 \times 10^8$ cfc/mL were added and incubated at 37° C. for 48 hours.

In Examples 1 through 19, a synergistic effect was demonstrated by testing the combination of methylene-bis (thiocyanate), designated as component A, and the corresponding organic acid, its salt or ester, designated as component B, in a series of tests in varying ratios and a range of concentrations against the fungus *Trichoderma harzianum* and also against the bacterium *Pseudomonas aeruginosa*, using the methods described above.

For each component A and B in a mixture containing A and B and for each component A and B acting alone, the lowest concentration which completely prevented growth of the fungi two weeks and the bacteria for 48 hours was determined. These concentrations were used as end points for synergism calculations. End points for the components alone or in mixtures described above were then compared with the end points for the pure active ingredients alone in similarly prepared flasks or test tubes.

Synergism was demonstrated by the method described by Kull, E. C., Eisman, P. C., Sylwestrwicz, H. D., and Mayer, R. L. 1961. Applied Microbiology. 9:538–541 wherein:

$QA/Qa + QB/Qb$ is less than 1

Qa=Concentration of compound A in parts per million, acting alone, which produced an end point.

Qb=Concentration of compound B in parts per million, acting alone, which produced an end point.

QA=Concentration of compound A in parts per million, in the mixture, which produced an end point.

QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is widely used and accepted. More detailed information is provided in the article by Kull et. al. Further information concerning this procedure is contained in U.S. Pat. No. 3,231,509, which disclosure is fully incorporated by reference.

The Examples demonstrate that in almost all of the samples, the combination of MTC with a corresponding organic acid produced a synergistic result (indicated by a ratio value of less than one.) There were a few samples, such as Table 2, <1.25 or <1.5, where synergistic results were inconclusive because endpoints for the acids used alone were not determined.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

Example 1
Component A = MTC
Component B = Benzoic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 2.5 | — | 250 | 0.25 | 0.5 | 0.75 |
| | — | 5.0 | — | 25 | 0.5 | 0.05 | 0.55 |
| | — | 5.0 | — | 50 | 0.5 | 0.1 | 0.6 |
| | — | 5.0 | — | 100 | 0.5 | 0.2 | 0.7 |
| | — | 5.0 | — | 250 | <0.5 | <0.5 | <1 |
| | — | — | 500 | — | — | — | — |
| Pseudomonas aeruginosa | 1 | — | — | — | — | — | — |
| | — | 0.1 | — | 25 | 0.1 | 0.1 | 0.2 |
| | — | 0.1 | — | 50 | 0.1 | 0.2 | 0.3 |
| | — | 0.1 | — | 100 | 0.1 | 0.4 | 0.5 |
| | — | 0.25 | — | 25 | 0.25 | 0.1 | 0.35 |
| | — | 0.25 | — | 50 | 0.25 | 0.2 | 0.45 |
| | — | 0.25 | — | 100 | 0.25 | 0.4 | 0.65 |
| | — | 0.5 | — | 10 | 0.5 | 0.04 | 0.54 |
| | — | 0.5 | — | 25 | 0.5 | 0.1 | 0.6 |
| | — | 0.5 | — | 50 | 0.5 | 0.2 | 0.7 |
| | — | 0.5 | — | 100 | 0.5 | 0.4 | 0.9 |
| | — | — | 250 | — | — | — | — |

Example 2
Component A = MTC
Component B = Sodium benzoate
Test organism Quantities producind end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 5 | — | 500 | 0.5 | 0.25 | 0.75 |
| | — | 5 | — | 1000 | 0.5 | 0.5 | <1 |
| | — | 5 | — | 2000 | 0.5 | 1 | <1.5 |
| | — | — | >2000 | — | — | — | — |
| Pseudomonas aeruginosa | 1 | — | — | — | — | — | — |
| | — | 0.25 | — | 1000 | 0.25 | 1 | <1.25 |
| | — | 0.5 | — | 250 | 0.5 | 0.25 | 0.75 |
| | — | 0.5 | — | 500 | 0.5 | 0.5 | <1 |
| | — | 0.5 | — | 1000 | 0.5 | 1 | <1.5 |
| | — | — | >1000 | — | — | — | — |

Example 3
Component A = MTC
Component B = Sorbic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 0.5 | — | 500 | 0.05 | 0.5 | 0.55 |
| | — | 1 | — | 500 | 0.1 | 0.5 | 0.6 |
| | — | 2.5 | — | 250 | 0.25 | 0.25 | 0.5 |
| | — | 2.5 | — | 500 | 0.25 | 0.5 | 0.75 |
| | — | 5 | — | 25 | 0.5 | 0.03 | 0.53 |
| | — | 5 | — | 50 | 0.5 | 0.05 | 0.55 |
| | — | 5 | — | 100 | 0.5 | 0.1 | 0.6 |
| | — | 5 | — | 250 | 0.5 | 0.25 | 0.75 |
| | — | 5 | — | 500 | 0.5 | 0.5 | 1 |
| | — | — | 1000 | — | — | — | — |
| Pseudomonas aeruginosa | 1 | — | — | — | — | — | — |
| | — | 0.1 | — | 100 | 0.1 | 0.4 | 0.5 |
| | — | 0.25 | — | 100 | 0.25 | 0.4 | 0.65 |
| | — | 0.5 | — | 10 | 0.5 | 0.04 | 0.54 |
| | — | 0.5 | — | 25 | 0.5 | 0.1 | 0.6 |
| | — | 0.5 | — | 50 | 0.5 | 0.2 | 0.7 |
| | — | 0.5 | — | 100 | 0.5 | 0.4 | 0.9 |
| | — | — | 250 | — | — | — | — |

Example 4
Component A = MTC
Component B = Potassium sorbate
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 2.5 | — | 250 | 0.25 | 0.13 | 0.38 |
| | — | 2.5 | — | 500 | 0.25 | 0.25 | 0.5 |
| | — | 2.5 | — | 1000 | 0.25 | 0.5 | 0.75 |
| | — | 2.5 | — | 2000 | 0.25 | 1 | <1.25 |
| | — | 5 | — | 25 | 0.5 | 0.01 | 0.51 |
| | — | 5 | — | 50 | 0.5 | 0.03 | 0.53 |
| | — | 5 | — | 100 | 0.5 | 0.05 | 0.55 |
| | — | 5 | — | 250 | 0.5 | 0.13 | 0.68 |
| | — | 5 | — | 500 | 0.5 | 0.25 | 0.75 |
| | — | 5 | — | 1000 | 0.5 | 0.5 | <1 |
| | — | 5 | — | 2000 | 0.5 | 1 | <1.5 |
| | — | — | >2000 | — | — | — | — |
| Pseudomonas aeruginosa | 1 | — | — | — | — | — | — |
| | — | 0.5 | — | 500 | 0.5 | 0.5 | <1 |
| | — | 0.5 | — | 1000 | 0.5 | 1 | <1.5 |
| | — | — | 1000 | — | — | — | — |

Example 5
Component A = MTC
Component B = p-hydroxybenzoic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 2.5 | — | 1000 | 0.25 | 0.5 | 0.75 |
| | — | 2.5 | — | 2000 | 0.25 | 1 | 1.25 |
| | — | 5 | — | 25 | 0.5 | 0.01 | 0.51 |
| | — | 5 | — | 50 | 0.5 | 0.03 | 0.53 |
| | — | 5 | — | 100 | 0.5 | 0.05 | 0.55 |
| | — | 5 | — | 250 | 0.5 | 0.13 | 0.63 |
| | — | 5 | — | 500 | 0.5 | 0.25 | 0.75 |
| | — | 5 | — | 1000 | 0.5 | 0.5 | 1 |
| | — | 5 | — | 2000 | 0.5 | 1 | 1.5 |
| | — | — | >2000 | — | — | — | — |
| Pseudomonas aeruginosa | 1 | — | — | — | — | — | — |
| | — | 0.1 | — | 100 | 0.1 | 0.2 | 0.3 |
| | — | 0.1 | — | 250 | 0.1 | 0.5 | 0.6 |
| | — | 0.25 | — | 100 | 0.25 | 0.2 | 0.45 |
| | — | 0.25 | — | 250 | 0.25 | 0.5 | 0.75 |
| | — | 0.5 | — | 5 | 0.5 | 0.01 | 0.51 |
| | — | 0.5 | — | 10 | 0.5 | 0.02 | 0.52 |
| | — | 0.5 | — | 25 | 0.5 | 0.05 | 0.55 |
| | — | 0.5 | — | 50 | 0.5 | 0.1 | 0.6 |
| | — | 0.5 | — | 100 | 0.5 | 0.2 | 0.7 |
| | — | 0.5 | — | 250 | 0.5 | 0.5 | 1 |
| | — | — | 500 | — | — | — | — |

Example 6
Component A = MTC
Component B = Dehydroacetic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 2.5 | — | 50 | 0.25 | 0.1 | 0.35 |
| | — | 2.5 | — | 100 | 0.25 | 0.2 | 0.45 |
| | — | 2.5 | — | 250 | 0.25 | 0.5 | 0.75 |
| | — | 5 | — | 25 | 0.5 | 0.05 | 0.55 |
| | — | 5 | — | 50 | 0.5 | 0.1 | 0.6 |
| | — | 5 | — | 100 | 0.5 | 0.2 | 0.7 |
| | — | 5 | — | 250 | 0.5 | 0.5 | 1 |
| | — | — | 500 | — | — | — | — |
| Pseudomonas aeruginosa | 1 | — | — | — | — | — | — |
| | — | 0.25 | — | 100 | 0.25 | 0.4 | 0.65 |
| | — | 0.5 | — | 50 | 0.5 | 0.2 | 0.7 |
| | — | 0.5 | — | 100 | 0.5 | 0.4 | 0.9 |
| | — | — | 250 | — | — | — | — |

Example 7
Component A = MTC
Component B = Propionic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 5 | — | 50 | 0.5 | 0.03 | 0.53 |
| | — | 5 | — | 100 | 0.5 | 0.05 | 0.55 |
| | — | 5 | — | 250 | 0.5 | 0.13 | 0.63 |
| | — | 5 | — | 500 | 0.5 | 0.25 | 0.75 |
| | — | 5 | — | 1000 | 0.5 | 0.5 | <1 |
| | — | — | 2000 | — | — | — | — |
| Pseudomonas aeruginosa | 1 | — | — | — | — | — | — |
| | — | 0.25 | — | 100 | 0.25 | 0.4 | 0.65 |
| | — | 0.5 | — | 50 | 0.5 | 0.2 | 0.7 |
| | — | 0.5 | — | 100 | 0.5 | 0.4 | 0.9 |
| | — | — | 250 | — | — | — | — |

Example 8
Component A = MTC
Component B = Methyl paraben
Test organism Quantities producing end points

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 1 | — | 500 | 0.1 | 0.5 | 0.6 |
| | — | 2.5 | — | 50 | 0.25 | 0.05 | 0.3 |
| | — | 2.5 | — | 100 | 0.25 | 0.1 | 0.35 |
| | — | 2.5 | — | 250 | 0.25 | 0.25 | 0.5 |
| | — | 2.5 | — | 500 | 0.25 | 0.5 | 0.75 |
| | — | 5 | — | 25 | 0.5 | 0.03 | 0.53 |
| | — | 5 | — | 50 | 0.5 | 0.05 | 0.55 |
| | — | 5 | — | 100 | 0.5 | 0.1 | 0.6 |
| | — | 5 | — | 250 | 0.5 | 0.25 | 0.75 |
| | — | 5 | — | 500 | 0.5 | 0.5 | <1 |
| | — | — | 1000 | — | — | — | — |
| Pseudomonas aeruginosa | 1 | — | — | — | — | — | — |
| | — | 0.1 | — | 1000 | 0.1 | 1 | 1.1 |
| | — | 0.25 | — | 500 | 025 | 0.5 | 0.75 |
| | — | 0.25 | — | 1000 | 0.25 | 1 | 1.25 |
| | — | 0.5 | — | 50 | 0.5 | 0.05 | 0.55 |
| | — | 0.5 | — | 100 | 0.5 | 0.1 | 0.6 |
| | — | 0.5 | — | 250 | 0.5 | 0.25 | 0.75 |
| | — | 0.5 | — | 500 | 0.5 | 0.5 | <1 |
| | — | 0.5 | — | 1000 | 0.5 | 1 | 1.5 |
| | — | — | >1000 | — | — | — | — |

Example 9
Component A = MTC
Component B = Propyl paraben
Test organism Quantities producing end points

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 1 | — | 250 | 0.1 | 0.5 | 0.6 |
| | — | 2.5 | — | 50 | 0.25 | 0.1 | 0.35 |
| | — | 2.5 | — | 100 | 0.25 | 0.2 | 0.45 |
| | — | 2.5 | — | 250 | 0.25 | 0.5 | 0.75 |
| | — | 2.5 | — | 25 | 0.5 | 0.05 | 0.55 |
| | — | 5 | — | 50 | 0.5 | 0.1 | 0.6 |
| | — | 5 | — | 100 | 0.5 | 0.2 | 0.7 |
| | — | 5 | — | 250 | 0.5 | 0.5 | 1 |
| | — | — | 500 | — | — | — | — |
| Pseudomonas aeruginosa | 1 | — | — | — | — | — | — |
| | — | 0.1 | — | 500 | 0.1 | 0.5 | 0.6 |
| | | 0.1 | — | 1000 | 0.1 | 1 | <1.1 |
| | — | 0.25 | — | 250 | 0.25 | 0.25 | 0.5 |
| | — | 0.25 | — | 500 | 0.25 | 0.5 | 0.75 |
| | — | 0.5 | — | 5 | 0.5 | 0.00 | |
| | — | 0.5 | — | 10 | 0.5 | 0.01 | 0.5 |
| | — | 0.5 | — | 25 | 0.5 | 0.03 | 0.53 |
| | — | 0.5 | — | 50 | 0.5 | 0.05 | 0.55 |
| | — | 0.5 | — | 100 | 0.5 | 0.1 | 0.6 |
| | — | 0.5 | — | 250 | 0.5 | 0.25 | 0.75 |
| | — | 0.5 | — | 500 | 0.5 | 0.5 | <1 |
| | — | — | >1000 | — | — | — | — |

Example 10
Component A = MTC
Component B = Nonanoic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 2.5 | — | 250 | 0.25 | 0.5 | 0.75 |
| | — | 5 | — | 100 | 0.5 | 0.2 | 0.7 |
| | — | 5 | — | 250 | 0.5 | 0.5 | <1 |
| | — | — | 500 | — | — | — | — |
| Pseudomonas aeruginosa | 1 | — | — | — | — | — | — |
| | — | 0.25 | — | 100 | 0.25 | 0.4 | 0.65 |
| | — | 0.5 | — | 5 | 0.5 | 0.02 | 0.52 |
| | — | 0.5 | — | 10 | 0.5 | 0.04 | 0.54 |
| | — | 0.5 | — | 25 | 0.5 | 0.1 | 0.6 |
| | — | 0.5 | — | 50 | 0.5 | 0.2 | 0.7 |
| | — | 0.5 | — | 100 | 0.5 | 0.25 | 0.75 |
| | — | — | 250 | — | — | — | — |

Example 11
Component A = MTC
Component B = Octanoic acid
Test organism Quantities producing end points (ppm)

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 2.5 | — | 50 | 0.25 | 0.1 | 0.35 |
| | — | 2.5 | — | 100 | 0.25 | 0.2 | 0.45 |
| | — | 2.5 | — | 250 | 0.25 | 0.5 | 0.75 |
| | — | 5 | — | 25 | 0.5 | 0.05 | 0.55 |
| | — | 5 | — | 50 | 0.5 | 0.1 | 0.6 |
| | — | 5 | — | 100 | 0.5 | 0.2 | 0.7 |
| | — | 5 | — | 250 | 0.5 | 0.5 | <1 |
| | — | — | 500 | — | — | — | — |
| Pseudomonas aeruginosa | 1 | — | — | — | — | — | — |
| | — | 0.25 | — | 100 | 0.25 | 0.4 | 0.65 |
| | — | 0.5 | — | 50 | 0.5 | 0.2 | 0.7 |
| | — | 0.5 | — | 100 | 0.5 | 0.4 | 0.9 |
| | — | — | 250 | — | — | — | — |

Example 12
Component A = MTC
Component B = Undecylenic acid
Test organism Quantities producing end points

| | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma harzianum | 10 | — | — | — | — | — | — |
| | — | 0.5 | — | 500 | 0.05 | 0.25 | 0.3 |
| | — | 0.5 | — | 1000 | 0.05 | 0.5 | 0.55 |
| | — | 1 | — | 500 | 0.1 | 0.25 | 0.35 |
| | — | 1 | — | 1000 | 0.1 | 0.5 | 0.6 |
| | — | 2.5 | — | 50 | 0.25 | 0.03 | 0.28 |
| | — | 2.5 | — | 100 | 0.25 | 0.05 | 0.30 |
| | — | 2.5 | — | 500 | 0.25 | 0.25 | 0.5 |
| | — | 5 | — | 25 | 0.5 | 0.01 | 0.51 |
| | — | 5 | — | 50 | 0.5 | 0.03 | 0.53 |
| | — | 5 | — | 100 | 0.5 | 0.05 | 0.55 |
| | — | 5 | — | 250 | 0.5 | 0.13 | 63 |
| | — | 5 | — | 500 | 0.5 | 0.25 | 0.75 |
| | — | — | 2000 | — | — | — | — |
| Pseudomonas aeruginosa | 1 | — | — | — | — | — | — |
| | — | 0.1 | — | 250 | 0.1 | 0.25 | 0.35 |
| | — | 0.1 | — | 500 | 0.1 | 0.5 | 0.6 |
| | — | 0.25 | — | 250 | 0.25 | 0.25 | 0.5 |
| | — | 0.25 | — | 500 | 0.25 | 0.5 | 0.75 |
| | — | 0.5 | — | 100 | 0.5 | 0.1 | 0.6 |
| | — | 0.5 | — | 250 | 0.5 | 0.25 | 0.75 |

Example 13
Component A = MTC
Component B = Lauric acid
Test organism Quantities producing end points (ppm)

|  | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma | 10 | — | — | — | — | — | — |
| harzianum | — | 2.5 | — | 500 | 0.25 | 0.25 | 0.5 |
|  | — | 2.5 | — | 1000 | 0.25 | 0.5 | 0.75 |
|  | — | 2.5 | — | 2000 | 0.25 | 0.1 | 1.25 |
|  | — | 5 | — | 25 | 0.5 | 0.01 | 0.51 |
|  | — | 5 | — | 50 | 0.5 | 0.03 | 0.53 |
|  | — | 5 | — | 100 | 0.5 | 0.05 | 0.55 |
|  | — | 5 | — | 250 | 0.5 | 0.13 | 0.68 |
|  | — | 5 | — | 500 | 0.5 | 0.25 | 0.75 |
|  | — | 5 | — | 1000 | 0.5 | 0.5 | 1 |
|  | — | 5 | — | 2000 | 0.5 | 1 | 1.5 |
|  | — | — | >2000 | — | — | — | — |
| Pseudomonas | 1 | — | — | — | — | — | — |
| aeruginosa | — | 0.25 | — | 500 | 0.25 | 0.5 | 0.75 |
|  | — | 0.25 | — | 1000 | 0.25 | 1 | 1.25 |
|  | — | 0.5 | — | 100 | 0.5 | 0.1 | 0.6 |
|  | — | 0.5 | — | 250 | 0.5 | 0.25 | 0.75 |
|  | — | 0.5 | — | 500 | 0.5 | 0.5 | <1 |
|  | — | 0.5 | — | 1000 | 0.5 | 1 | 1.5 |
|  | — | — | >1000 | — | — | — | — |

Example 14
Component A = MTC
Component B = Formic acid
Test organism Quantities producing end points (ppm)

|  | $Q_a$ | $Q_A$ | $Q_b$ | $Q_B$ | $Q_A/Q_a$ | $Q_b/Q_B$ | $Q_A/Q_a + Q_B/Q_b$ |
|---|---|---|---|---|---|---|---|
| Trichoderma | 10 | — | — | — | — | — | — |
| harzianum | — | 2.5 | — | 2000 | 0.25 | 1 | <1.25 |
|  | — | 5 | — | 250 | 0.5 | 0.13 | 0.63 |
|  | — | 5 | — | 500 | 0.5 | 0.25 | 0.75 |
|  | — | 5 | — | 1000 | 0.5 | 0.5 | <1 |
|  | — | 5 | — | 2000 | 0.5 | 1 | <1.5 |
|  | — | — | >2000 | — | — | — | — |
| Pseudomonas | 1 | — | — | — | — | — | — |
| aeruginosa | — | 0.25 | — | 50 | 0.25 | 0.5 | 0.75 |
|  | — | 0.5 | — | 50 | 0.5 | 0.5 | <1 |
|  | — | — | 100 | — | — | — | — |

Example 15
Component A = MTC
Component B = Acetic acid
Test organism Quantities producing end points (ppm)

|  | $Q_a$ | $Q_A$ | $Q_b$ | $Q_B$ | $Q_A/Q_a$ | $Q_b/Q_B$ | $Q_A/Q_a + Q_B/Q_b$ |
|---|---|---|---|---|---|---|---|
| Trichoderma | 10 | — | — | — | — | — | — |
| harzianum | — | 1 | — | 2000 | 0.1 | 1 | <1.1 |
|  | — | 2.5 | — | 2000 | 0.25 | 1 | <1.25 |
|  | — | 5 | — | 500 | 0.5 | 0.25 | 0.75 |
|  | — | 5 | — | 1000 | 0.5 | 0.5 | <1 |
|  | — | 5 | — | 2000 | 0.5 | 1 | <1.5 |
|  | — | — | >2000 | — | — | — | — |
| Pseudomonas | 1 | — | — | — | — | — | — |
| aeruginosa | — | 0.25 | — | 50 | 0.25 | 0.5 | 0.75 |
|  | — | 0.5 | — | 50 | 0.5 | 0.5 | <1 |
|  | — | — | 100 | — | — | — | — |

Example 16
Component A = MTC
Component B = Oxalic acid
Test organism Quantities producing end points (ppm)

|  | $Q_a$ | $Q_A$ | $Q_b$ | $Q_B$ | $Q_A/Q_a$ | $Q_b/Q_B$ | $Q_A/Q_a + Q_B/Q_b$ |
|---|---|---|---|---|---|---|---|
| Trichoderma | 10 | — | — | — | — | — | — |
| harzianum | — | 5 | — | 1000 | 0.5 | 0.5 | <1 |
|  | — | 5 | — | 2000 | 0.5 | 1 | <1.5 |
|  | — | — | >2000 | — | — | — | — |
| Pseudomonas | 1 | — | — | — | — | — | — |
| aeruginosa | — | 0.25 | — | 100 | 0.25 | 0.4 | 0.65 |
|  | — | 0.5 | — | 25 | 0.5 | 0.1 | 0.6 |
|  | — | 0.5 | — | 50 | 0.5 | 0.2 | 0.7 |
|  | — | 0.5 | — | 100 | 0.5 | 0.4 | 0.9 |
|  | — | — | 250 | — | — | — | — |

Example 17
Component A = MTC
Component B = Citric acid
Test organism Quantities producing end points (ppm)

|  | $Q_a$ | $Q_A$ | $Q_b$ | $Q_B$ | $Q_A/Q_a$ | $Q_b/Q_B$ | $Q_A/Q_a + Q_B/Q_b$ |
|---|---|---|---|---|---|---|---|
| Trichoderma | 10 | — | — | — | — | — | — |
| harzianum | — | 5 | — | 1000 | 0.5 | 0.5 | <1 |
|  | — | 5 | — | 2000 | 0.5 | 1 | <1.5 |
|  | — | — | >2000 | — | — | — | — |
| Pseudomonas | 1 | — | — | — | — | — | — |
| aeruginosa | — | 0.25 | — | 100 | 0.25 | 0.4 | 0.65 |
|  | — | 0.5 | — | 25 | 0.5 | 0.1 | 0.6 |
|  | — | 0.5 | — | 50 | 0.5 | 0.2 | 0.7 |
|  | — | — | 250 | — | — | — | — |

Example 18
Component A = MTC
Component B = Malic acid
Test organism Quantities producing end points (ppm)

|  | $Q_a$ | $Q_A$ | $Q_b$ | $Q_B$ | $Q_A/Q_a$ | $Q_b/Q_B$ | $Q_A/Q_a + Q_B/Q_b$ |
|---|---|---|---|---|---|---|---|
| Trichoderma | 10 | — | — | — | — | — | — |
| harzianum | — | 5 | — | 1000 | 0.5 | 0.5 | <1 |
|  | — | 5 | — | 2000 | 0.5 | 1 | <1.5 |
|  | — | — | >2000 | — | — | — | — |
| Pseudomonas | 1 | — | — | — | — | — | — |
| aeruginosa | — | 0.25 | — | 100 | 0.25 | 0.4 | 0.65 |
|  | — | 0.5 | — | 50 | 0.5 | 0.2 | 0.7 |
|  | — | 0.5 | — | 100 | 0.5 | 0.4 | 0.9 |
|  | — | — | 250 | — | — | — | — |

Example 19
Component A = MTC
Component B = Glycolic acid
Test organism Quantities producing end points (ppm)

|  | $Q_a$ | $Q_A$ | $Q_b$ | $Q_B$ | $Q_A/Q_a$ | $Q_b/Q_B$ | $Q_A/Q_a + Q_B/Q_b$ |
|---|---|---|---|---|---|---|---|
| Trichoderma | 10 | — | — | — | — | — | — |
| harzianum | — | 5 | — | 1000 | 0.5 | 0.5 | <1 |
|  | — | 5 | — | 2000 | 0.5 | 1 | <1.5 |
|  | — | — | >2000 | — | — | — | — |

-continued

Example 19
Component A = MTC
Component B = Glycolic acid
Test organism Quantities producing end points (ppm)

| | $Q_a$ | $Q_A$ | $Q_b$ | $Q_B$ | $Q_a/Q_A$ | $Q_b/Q_B$ | $Q_A/Q_a$ + $Q_B/Q_b$ |
|---|---|---|---|---|---|---|---|
| Pseudomonas | 1 | — | — | — | — | — | — |
| aeruginosa | — | 0.25 | — | 100 | 0.25 | 0.4 | 0.65 |
| | — | 0.5 | — | 50 | 0.5 | 0.2 | 0.7 |
| | — | 0.5 | — | 100 | 0.5 | 0.4 | 0.9 |
| | — | — | 250 | — | — | — | — |

What is claimed is:

1. A composition to control the growth of at least one microorganism selected from the group consisting of bacteria, fungi, and mixtures thereof comprising a synergistic microbicidally effective mixture of (A) a methylene-bis(thiocyanate) and (B) at least one organic acid selected from the group consisting of undecylenic acid, lauric acid, oxalic acid, glycolic acid, citric acid, malic acid, their respective salts, and mixtures thereof.

2. The composition of claim 1, wherein said bacteria or fungi is *Trichoderma harzianum* or *Pseudomonas aeruginosa*.

3. The composition of claim 1, wherein the weight ratio of (A) to (B) is from about 0.01:99 to about 99:0.01.

4. The composition of claim 3, wherein the weight ratio of (A) to (B) is from about 1:30 to about 30:1.

5. The composition of claim 4, wherein the weight ratio of (A) to (B) is from about 1:5 to about 5:1.

6. The composition of claim 1, wherein the weight ratio of concentrations are from about 0.01 to about 3000 ppm of methylene-bis(thiocyanate), and from about 0.1 ppm to about 1% by weight of the organic acid.

7. The composition of claim 6, wherein the weight ratio of concentrations are from about 0.1 to about 1000 ppm of methylene-bis(thiocyanate), and from about 0.1 to about 5000 ppm of the organic acid.

8. The composition of claim 7, wherein the weight ratio of concentrations are from about 0.1 to about 500 ppm of methylene-bis(thiocyanate), and from about 0.1 to about 2000 ppm of the organic acid.

9. The composition of claim 1, wherein said organic acid is undecylenic acid or a salt thereof.

10. The composition of claim 1, wherein said organic acid is lauric acid or a salt thereof.

11. The composition of claim 1, wherein said organic acid is oxalic acid or a salt thereof.

12. The composition of claim 1, wherein said organic acid is glycolic acid or a salt thereof.

13. The composition of claim 1, wherein said organic acid is citric acid or a salt thereof.

14. The composition of claim 1, wherein said organic acid is malic acid or a salt thereof.

15. A method of controlling the growth of at least one microorganism selected from the group consisting of bacteria, fungi, and mixtures thereof in or on a product, material or medium susceptible to attack by said microorganism comprising the step of applying to said product, material or medium to control said growth a composition comprising a synergistic microbicidally effective mixture of (A) methylene-bis(thiocyanate) and (B) at least one organic acid selected from the group consisting of undecylenic acid, lauric acid, oxalic acid, glycolic acid, citric acid, malic acid, their respective salts, and mixtures thereof.

16. The method of claim 15, wherein said bacteria or fungi is *Trichoderma harzianum* or *Pseudomonas aeruginosa*.

17. The method of claim 15, wherein said product, material or medium is wood pulp, wood chips, lumber, paints, leather, adhesives coatings, animal hides, tanning liquors, paper mill liquors, metalworking fluids, petrochemicals, pharmaceutical formulations, cooling tower water, cosmetics, toiletry formulations, textiles, geological drilling lubricants or agrochemical compositions for crop or seed protection.

18. The method of claim 15, wherein said composition is in the form of a solid, dispersion, emulsion or solution.

19. The method of claim 15, wherein said components (A) and (B) are applied separately to the product, material or medium.

20. The method of claim 15, wherein said components (A) and (B) are first combined and then added to the product, material or medium.

21. The method of claim 15, wherein the weight ratio of concentrations are from about 0.01 to about 3000 ppm of methylene-bis(thiocyanate), and from about 0.1 ppm to about 1% by weight of the organic acid.

22. The method of claim 15, wherein the weight ratio of concentrations are from about 0.1 to about 1000 ppm of methylene-bis(thiocyanate), and from about 0.1 to about 5000 ppm of the organic acid.

23. The method of claim 15, wherein the weight ratio of concentrations are from about 0.1 to about 500 ppm of methylene-bis(thiocyanate), and from about 0.1 to about 2000 ppm of the organic acid.

24. The method of claim 15, wherein said organic acid is undecylenic acid or a salt thereof.

25. The method of claim 15, wherein said organic acid is lauric acid or a salt thereof.

26. The method of claim 15, wherein said organic acid is oxalic acid or a salt thereof.

27. The method of claim 15, wherein said organic acid is glycolic acid or a salt thereof.

28. The method of claim 15, wherein said organic acid is citric acid or a salt thereof.

29. The method of claim 15, wherein said organic acid is malic acid or a salt thereof.

30. A method for preventing spoilage of a product, material or medium caused by bacteria or fungi comprising the step of applying to said product, material or medium to prevent said spoilage, a composition comprising a synergistic microbicidally effective mixture of (A) methylene-bis(thiocyanate) and (B) at least one organic acid selected from the group consisting of undecylenic acid, lauric acid, oxalic acid, glycolic acid, citric acid, malic acid, their respective salts, and mixtures thereof.

31. The method of claim 30, wherein said material is seeds or crops.

32. The method of claim 30, wherein said organic acid is undecylenic acid or a salt thereof.

33. The method of claim 30, wherein said organic acid is lauric acid or a salt thereof.

34. The method of claim 30, wherein said organic acid is oxalic acid or a salt thereof.

35. The method of claim 30, wherein said organic acid is glycolic acid or a salt thereof.

36. The method of claim 30, wherein said organic acid is citric acid or a salt thereof.

37. The method of claim 30, wherein said organic acid is malic acid or a salt thereof.

* * * * *